United States Patent [19]

Sekine et al.

[11] Patent Number: 5,795,916
[45] Date of Patent: Aug. 18, 1998

[54] COMPOSITION OF EXTERNAL PREPARATION

[75] Inventors: Takashi Sekine; Eiji Ogura; Shinichi Ota; Kazuyuki Ishikawa, all of Ami-machi, Japan

[73] Assignee: Tsumura & Co., Tokyo, Japan

[21] Appl. No.: 776,700

[22] PCT Filed: Aug. 8, 1995

[86] PCT No.: PCT/JP95/01576

§ 371 Date: Apr. 21, 1997

§ 102(e) Date: Apr. 21, 1997

[87] PCT Pub. No.: WO96/04902

PCT Pub. Date: Feb. 22, 1996

[30] Foreign Application Priority Data

Aug. 9, 1994 [JP] Japan ..................... 6-206139

[51] Int. Cl.$^6$ ........................... A61K 31/19; A61K 31/16
[52] U.S. Cl. ................................... 514/567; 514/629
[58] Field of Search ........................ 514/567, 629

[56] References Cited

U.S. PATENT DOCUMENTS 5,176,916 1/1993 Yamanaka et al. .................. 424/448

FOREIGN PATENT DOCUMENTS 4-25929   6/1992   Japan .

OTHER PUBLICATIONS

Nakagawa et al., JP 62-228027 (1987) (Abstract).

*Primary Examiner*—Phyllis G. Spivack
*Attorney, Agent, or Firm*—Oblon, Spivak, McClelland, Maier & Neustadt, P.C.

[57] ABSTRACT

Disclosed herein is an external preparation composition, in a liquid preparation, cream, ointment or cataplasm plaster, characterized in that the composition contains a water-soluble salt of diclofenac, such as diclofenac sodium, water, and a fatty acid dialkylolamide and/or its polyoxyethylene adduct.

The external preparation composition according to this invention is excellent in the percutaneous absorption of the water-soluble salt of diclofenac, which has high solubility and stability in the preparation.

9 Claims, No Drawings

COMPOSITION OF EXTERNAL PREPARATION

TECHNICAL FIELD

This invention relates to an external preparation composition containing a water-soluble salt of diclofenac, and specifically to an external preparation composition which contains a water-soluble salt of diclofenac dissolved in a base and is useful as a medicinal preparation or the like having a stable composition and high absorption.

Background Art

Diclofenac sodium, which is a water-soluble salt of diclofenac, is one of medicines most widely used these days as non-steroidal anti-inflammatory analgesics and in clinics, is employed in the form of oral preparations or suppositories. Due to its strong drug efficacy, however, its use may be limited, for example, where there is a potential problem of a shock or gastrointestinal ulcer as a side effect by an abrupt rise in its blood concentration.

Numerous attempts have been made to date with a view to maintaining drug efficacies without side effects by percutaneously administering drugs. For example, Japanese Patent Application Laid-Open (Kokai) No. SHO 62-103015 discloses that incorporation of a fatty acid monoalkylolamide as a penetration enhancer in a drug-containing composition permits efficient absorption of the drug through a skin or mucosa.

The above patent application discloses diclofenac sodium as an illustrative drug, but contains only one working example directed to a diclofenac sodium composition which is an oil-base suppository. In this suppository composition, diclofenac sodium is evenly dispersed but is not completely dissolved.

On the other hand, Japanese Patent Application Laid-Open (Kokai) No. SHO 63-91318 discloses a diclofenac-sodium-containing plaster in which a crosslinked water-containing gel with diclofenac sodium and 1,3-butylene glycol dissolved therein is spread on a backing. Further, Japanese Patent Application Laid-Open (Kokai) No. HEI 3-291222 discloses a diclofenac-sodium-containing topical medicinal composition in the form of a clear gel, which does not contain any emulsified fat layer.

It is however still difficult to assure solubility and stability of the water-soluble salt of diclofenac in a preparation even by these techniques. It is the current situation that no one has succeeded yet in developing a stable external preparation having excellent absorption.

Under the above-described circumstances, it has been desired to develop an external preparation composition of diclofenac, which contains a water-soluble salt of diclofenac dissolved in a base, is stable without precipitation of diclofenac or its salt, and has high skin permeability of the active ingredient.

Disclosure of the Invention

With the foregoing circumstances in view, the present inventors have proceeded with an extensive investigation to develop an external preparation composition which maintains the solubility of a water-soluble salt of diclofenac in the preparation and is excellent in stability and skin permeability of the active ingredient. As a result, it has been found that dissolution of a water-soluble salt of diclofenac in an aqueous solution of a fatty acid dialkylolamide or its polyoxyethylene adduct can provide a stable preparation and can achieve the above-described object.

It has also been found that addition of a pharmaceutically-acceptable additive to an aqueous solution of the above preparation can further increase the solubility of the water-soluble salt of diclofenac in the preparation and the skin permeability of diclofenac, leading to the completion of the present invention.

Namely, the present invention provides an external preparation composition comprising a water-soluble salt of diclofenac, water, and a fatty acid dialkylolamide and/or a polyoxyethylene adduct thereof.

Best Modes for Carrying Out the Invention

Examples of the water-soluble salt of diclofenac, which is an active ingredient in the external preparation composition according to the present invention, include the sodium, potassium, pyrrolidine, piperidine, N-hydroxyethylpyrrolidine, N-hydroxyethylpiperidine, triethanolamine, diethanolamine, ethylenediamine and diethyl ammonium salts of diclofenac.

On the other hand, the fatty acid dialkylolamide, another essential ingredient of the external preparation composition according to the present invention, is a compound available by condensation of a fatty acid and a dialkylolamine. Illustrative of its fatty acid moiety include coconut oil fatty acid, palm kernel oil fatty acid, palmitic acid, myristic acid, stearic acid, lauric acid, oleic acid, linoleic acid, isostearic acid, capric acid, and caprylic acid. Examples of the dialkylolamine moiety to be condensed include di(lower alkanol)amine such as diethanolamine and diisopropanolamine. These fatty acid dialkylolamide can be used either singly or in combination. Further, the polyoxyethylene adduct of the fatty acid dialkylolamide is available by adding ethylene oxide to hydroxyl groups of the fatty acid dialkylolamide, and the number of moles of the added ethylene oxide ranges from 1 to 10.

Preferred examples of the fatty acid dialkylolamide include coconut fatty acid diethanolamide, palm kernel fatty acid diethanolamide, stearic acid diethanolamide, lauric acid diethanolamide, oleic acid diethanolamide, linoleic acid diethanolamide and isostearic acid diethanolamide, and as the ethylene oxide of the fatty acid dialkylolamide, the ethylene oxide adducts of these compounds are preferred. Of these, particularly preferred are coconut fatty acid diethanolamide, lauric acid diethanolamide and stearic acid diethanolamide.

The external preparation composition according to the present invention can be prepared by mixing the water-soluble salt of diclofenac, water and the above-described ingredients and then formulating the resulting mixture into a dosage form in a manner known per se in the art.

According to one example of a process for the preparation of the external preparation composition of the present invention, the fatty acid dialkylolamide and the water-soluble salt of diclofenac are added to and dissolved in purified water, whereby an aqueous solution of the water-soluble salt of diclofenac is prepared. Other additives are then added as needed, followed by the preparation of the resultant mixture into a desired dosage form.

Concerning the amount of the water-soluble salt of diclofenac to be added in the external preparation composition according to the present invention, it is only necessary to add the water-soluble salt in an amount sufficient to bring about desired effects in accordance with the purpose of the administration. In general, it can be added in an amount of from 0.05 to 5 wt. %. An amount of the water-soluble salt of diclofenac smaller than 0.05 wt. % is not expected to bring about sufficient pharmacological effects, whereas an amount greater than 5 wt. % results in a lowered absorption ratio because such a great amount is in excess of the absorption limit.

Regarding the amount of the fatty acid dialkylolamide or the ethylene oxide adduct thereof, it is preferred to add the same so that they amount in total to 0.01 to 10 wt. % based on the weight of the external preparation composition according to the present invention. Addition in a range of from 0.1 to 5 wt. % is particularly preferred. An amount of the fatty acid dialkylolamide small than 0.01 wt. % leads to a reduction in the solubility of diclofenac or its salt, whereas an amount greater than 10 wt. % causes the problem of irritation.

The pH of the external preparation composition according to the present invention, on the other hand, is preferably from 7 to 9, with pH 7.5 to pH 8.5 being particularly preferred. A pH lower than 7 causes the problem that the water-soluble salt of diclofenac such as diclofenac sodium becomes diclofenac and crystallizes out in the external preparation composition, while a pH higher than 9 develops the problem that the water-soluble salt of diclofenac becomes unstable.

To adjust the pH of the composition, it is only necessary to increase or decrease the amount of the fatty acid dialkylolamide to be added. It is however possible to adjust the pH by adding a pH regulator to be described subsequently herein.

The external preparation composition according to the present invention can be formulated into a preparation form which is commonly employed as a preparation form for external preparations. Advantageously usable preparation forms include, but are not limited specifically to, various solutions, ointments, creams, cataplasm plasters, and the like.

In the external preparation composition according to the present invention, it is also possible to use, depending on the preparation form, various additives which have been commonly used to date.

These additives can include the followings:

Hydrophilic Polymers

A hydrophilic polymer can serve as a base for the external preparation composition according to the present invention, and in solutions and creams, enhances adhesion to the skin. Illustrative of the hydrophilic polymer include carboxymethylcellulose and salts thereof, polyacrylic acid and salts thereof, carboxyvinyl polymers and salts thereof, alginic acid and salts thereof, propylene glycol alginate, chitosan, hydroxypropylcellulose, hydroxypropylmethylcellulose, hydroxyethylcellulose, ethylcellulose, methylcellulose, polyvinyl alcohol, polyvinyl pyrrolidone, N-vinylacetamide polymer, polyvinyl methacrylate, polyethylene glycol, pluronic, gelatin, methyl vinyl ether-maleic anhydride copolymer, soluble starch, pullulan and a copolymer of methyl acrylate and 2-ethylhexyl acrylate.

Polyhydric Alcohols

A polyhydric alcohol enhances the solubility and moisture-retaining property of the external preparation composition according to the present invention. Illustrative of the polyhydric alcohol are propylene glycol, 1,3-butylene glycol, glycerin, sorbitol, and mannitol.

Additives to a Base

An additive is a substance which can be added together with the above-described hydrophilic polymer to a base of an external preparation. Illustrative additives for cataplasms include kaolin, light anhydrous silicic acid, silicon dioxide hydrate, silicic anhydride, magnesium metasilicate aluminate, aluminum hydroxide, magnesium hydroxide, synthetic aluminum silicate, talc, bentonite, calcium carbonate, titanium oxide, aluminum glycinate, and zinc oxide; for ointments, cetanol, stearyl alcohol, cetostearyl alcohol, stearic acid, white petrolatum, hydrophilic ointments, light anhydrous silicic acid, silicon dioxide hydrate, silicic anhydride, titanium oxide, and zinc oxide; and for solutions, cetanol, stearyl alcohol, cetostearyl alcohol, stearic acid, light anhydrous silicic acid, silicon dioxide hydrate, silicic anhydride, and titanium oxide.

Stabilizers

Illustrative stabilizers include sodium edetate, citric acid, sodium citrate, oxybenzone, ascorbic acid, tocopherol, dibutylhydroxytoluene, butylhydroxyanisole, propyl gallate, and sodium hydrogensulfite. pH regulators:

Illustrative pH regulators include tartaric acid, citric acid, malic acid, lactic acid, hydrochloric acid, phosphoric acid, acetic acid, fumaric acid, maleic acid, sodium hydroxide, ammonia, urea, ethylenediamine, diisopropanolamine, diethanolamine, tri-isopropanolamine, and triethanolamine.

Penetration Enhancers

Illustrative penetration enhancers include ethanol, isopropyl alcohol, lauryl alcohol, oleyl alcohol, octyldodecanol, isopropyl myristate, diisopropyl adipate, diethyl sebacate, diisopropyl sebacate, propylene glycol caprate, medium-chain fatty acid triglyceride, and squalane.

Emulsifying Agents

Illustrative emulsifying agents include, lecithin, lecithin derivatives, propylene glycol fatty acid esters, glycerin fatty acid esters, sorbitan fatty acid esters, polyoxyethylene sorbitan fatty acid esters, polyethylene glycol fatty acid esters, polyoxyethylene hydrated castor oil, polyoxyethylene alkyl ethers, and pluronic.

Antiseptics

Illustrative antiseptics include parabens such as methylparaben, ethylparaben and propylparaben; benzyl alcohol; benzalconium chloride; benzethonium chloride; and chlorobutanol.

In the external preparation composition according to the present invention, the particularly preferred application form is a cataplasm which is available by spreading the composition as a cataplasm plaster over a backing such as a fabric or a non-woven fabric.

When employed as a cataplasm plaster, it is preferred to add the above-described polyhydric alcohol so that its content ranges from 0.01 to 80 wt. % or so based on the weight of the external preparation composition according to the present invention, with a range of from 0.1 to 50 wt. % being particularly preferred. A content of the polyhydric alcohol lower than 0.01 wt. % leads to a reduction in moisture-retaining property, whereas a content higher than 80 wt. % results in stronger irritation. It is also preferred to add a polyhydric alcohol at a similar content when the preparation form is a solution.

When the external preparation composition according to the present invention is used as a cataplasm plaster, it is preferred to add the above-described hydrophilic polymer so that its content ranges from 0.01 to 50 wt. % or so based on the weight of the external preparation composition according to the present invention, with a range of from 0.1 to 30 wt. % being particularly preferred. A content of the hydrophilic polymer lower than 0.01 wt. % makes it very difficult to form the cataplasm plaster into a semi-solid preparation, whereas a content higher than 50 wt. % results in higher viscosity and lower absorption.

The external preparation composition according to the present invention, which has been obtained as described above, can be advantageously used as an external anti-inflammatory analgesic, anti-suntan cosmetic or the like because, as will be described subsequently herein, the water-soluble salt of diclofenac is stably dissolved in the preparation and moreover, the percutaneous absorption of the active ingredient is excellent.

The present invention will next be described in detail by the following Invention Examples and Comparative Examples. It is however to be bone in mind that the present invention is by no means limited by them.

EXAMPLE 1

Lotion

| (Composition) | (wt. %) |
| --- | --- |
| Diclofenac sodium | 2.0 |
| Lauric acid diethanolamide | 2.0 |
| Hydroxypropylcellulose | 0.5 |
| Pluronic F-68 | 1.0 |
| Propylene glycol | 2.0 |
| Isostearyl alcohol | 5.0 |
| Oxybenzone | 0.5 |
| Methylparaben | 0.15 |
| Propylparaben | 0.05 |
| Purified water | 86.8 |
| Total | 100.0 |

(Procedures)

The diclofenac sodium and lauric acid diethanolamide were added to the purified water so that a homogeneous solution was prepared. The remaining additives were added to the solution, followed by emulsification in a homomixer to prepare a preliminary solution. The preliminary solution was then treated five times at 300 kg/cm$^2$ in a Manton-Gaulin homogenizer, whereby an emulsified lotion was obtained.

EXAMPLE 2

Ointment

| (Composition) | (wt. %) |
| --- | --- |
| Diclofenac sodium | 2.0 |
| Lauric acid diethanolamide | 1.0 |
| Coconut fatty acid diethanolamide | 1.0 |
| Polysorbate 60 | 3.0 |
| Cetanol | 4.0 |
| Stearyl alcohol | 5.0 |
| Octyldodecanol | 5.0 |
| Medium-chain fatty acid triglyceride | 6.0 |
| Sorbitol | 10.0 |
| Butylhydroxyanisole | 0.01 |
| Methylparaben | 0.1 |
| Propylparaben | 0.1 |
| Purified water | 62.79 |
| Total | 100.0 |

(Procedures)

The diclofenac sodium, lauric acid diethanolamide and coconut fatty acid diethanolamide were added to and dissolved in the purified water, followed by the further addition of the polysorbate 60, sorbitol and methylparaben. The resultant mixture was heated and dissolved at about 75° C. to provide a water layer. On the side, as an oil layer, the cetanol, stearyl alcohol, octyldodecanol, medium-chain fatty acid triglyceride, butylhydroxyanisole and propylparaben were heated and melted at about 75° C.

The water layer and oil layer were emulsified using a vacuum emulsifier and then deaerated and cooled, whereby an emulsified homogeneous ointment was obtained.

EXAMPLE 3

Cataplasm

| (Composition) | (wt. %) |
| --- | --- |
| Diclofenac sodium | 2.0 |
| Sodium polyacrylate | 4.0 |
| Carmellose sodium | 2.0 |
| Hydroxypropylmethylcellulose | 2.0 |
| Coconut fatty acid diethanolamide | 2.0 |
| Oleyl alcohol | 1.0 |
| 1,3-Butylene glycol | 10.0 |
| 70% Sorbitol solution | 30.0 |
| Aluminum glycinate | 0.2 |
| Tartaric acid | 0.3 |
| Purified water | 46.5 |
| Total | 100.0 |

(Procedures)

The diclofenac sodium, coconut fatty acid diethanolamide and hydroxypropylmethylcellulose were added to the purified water so that a homogeneous solution was obtained. The remaining additives were added to the solution, and the resultant mixture was stirred into a homogeneous gel. The gel was spread at a uniform thickness over a non-woven fabric, whereby a cataplasm was obtained.

EXAMPLE 4

Lotion

| (Composition) | (wt. %) |
| --- | --- |
| Diclofenac sodium | 3.0 |
| Lauric acid diethanolamide | 2.0 |
| Hydroxypropylcellulose | 0.5 |
| Pluronic F-68 | 1.0 |
| Propylene glycol | 2.0 |
| Lauryl alcohol | 5.0 |
| Oxybenzone | 0.5 |
| Methylparaben | 0.15 |
| Propylparaben | 0.05 |
| Purified water | 85.8 |
| Total | 100.0 |

(Procedures)

The diclofenac sodium and lauric acid diethanolamide were added to the purified water so that a homogeneous solution was prepared. The remaining additives were added to the solution, followed by emulsification in a homomixer to prepare a preliminary solution. The preliminary solution was then treated five times at 300 kg/cm$^2$ in a Manton-Gaulin homogenizer, whereby an emulsified lotion was obtained.

EXAMPLE 5

Ointment

| (Composition) | (wt. %) |
|---|---|
| Diclofenac sodium | 3.0 |
| Lauric acid diethanolamide | 1.0 |
| Coconut fatty acid diethanolamide | 1.0 |
| Polysorbate 60 | 3.0 |
| Cetanol | 4.0 |
| Stearyl alcohol | 5.0 |
| Octyldodecanol | 5.0 |
| Squalane | 6.0 |
| Sorbitol | 10.0 |
| Butylhydroxyanisole | 0.01 |
| Methylparaben | 0.1 |
| Propylparaben | 0.1 |
| Purified water | 61.79 |
| Total | 100.0 |

(Procedures)

The diclofenac sodium, lauric acid diethanolamide and coconut fatty acid diethanolamide were added to and dissolved in the purified water, followed by the further addition of the polysorbate 60, sorbitol and methylparaben. The resultant mixture was heated and dissolved at about 75° C. to provide a water layer. On the side, as an oil layer, the cetanol, stearyl alcohol, octyldodecanol, medium-chain fatty acid triglyceride, butylhydroxyanisole and propylparaben were heated and melted at about 75° C.

The water layer and oil layer were emulsified using a vacuum emulsifier and then deaerated and cooled, whereby an emulsified homogeneous ointment was obtained.

EXAMPLE 6

Ointment

| (Composition) | (wt. %) |
|---|---|
| Diclofenac sodium | 3.00 |
| Coconut fatty acid diethanolamide | 4.00 |
| Glycerin | 5.00 |
| Isopropyl alcohol | 30.00 |
| Hydroxyethylcellulose | 2.00 |
| Methylcellulose | 2.00 |
| Oleyl alcohol | 1.00 |
| Oxybenzone | 0.50 |
| Methylparaben | 0.15 |
| Propylparaben | 0.50 |
| Purified water | 51.85 |
| Total | 100.0 |

(Procedures)

The coconut fatty acid diethanolamide and diclofenac sodium were added to the purified water so that a homogeneous solution was prepared. To the solution, the isopropyl alcohol, glycerin, oxybenzone, methylparaben and propylparaben were added, followed by stirring. The hydroxyethylcellulose and methylcellulose were added further. The resultant mixture was stirred thoroughly, whereby a homogeneous gel ointment was obtained.

EXAMPLE 7

Cataplasm

| (Composition) | (wt. %) |
|---|---|
| Diclofenac sodium | 1.00 |
| Sodium polyacrylate | 4.00 |
| Carmellose sodium | 2.00 |
| Hydroxypropylmethylcellulose | 2.00 |
| Lauric acid diethanolamide | 2.00 |
| Lauryl alcohol | 1.00 |
| Propylene glycol | 10.00 |
| 70% Sorbitol solution | 30.00 |
| Aluminum hydroxide | 0.20 |
| Tartaric acid | 0.30 |
| Purified water | 47.50 |
| Total | 100.0 |

(Procedures)

The diclofenac sodium and lauric acid diethanolamide were added to the purified water so that a homogeneous solution was obtained. The 70% sorbitol solution and lauryl alcohol were added to the solution, and the resultant mixture was stirred into a homogeneous solution. The remaining additives were then dispersed in the propylene glycol. The resultant dispersion was added to the previously-prepared solution, and the mixture so obtained was stirred to obtain a homogeneous gel. The gel was spread at a uniform thickness over a non-woven fabric, whereby a cataplasm was obtained.

EXAMPLE 8

Cataplasm

| (Composition) | (wt. %) |
|---|---|
| Diclofenac sodium | 2.0 |
| Light anhydrous silicic acid | 2.0 |
| Sodium polyacrylate | 4.0 |
| Carmellose sodium | 2.0 |
| Hydroxypropylmethylcellulose | 2.0 |
| Coconut fatty acid diethanolamide | 2.0 |
| Oleyl alcohol | 1.0 |
| 1,3-Butylene glycol | 10.0 |
| 70% Sorbitol solution | 30.0 |
| Aluminum glycinate | 0.2 |
| Tartaric acid | 0.3 |
| Purified water | 44.5 |
| Total | 100.0 |

(Procedures)

The diclofenac sodium, coconut fatty acid diethanolamide and hydroxypropylmethylcellulose were added to the purified water so that a homogeneous solution was obtained. The remaining additives were added to the solution, followed by stirring to obtain a homogeneous gel. The gel was spread at a uniform thickness over a non-woven fabric, whereby a cataplasm was obtained.

Comparative Example 1

Lotion

A lotion was prepared in a similar manner as in Example 1 except for the exclusion of lauric acid diethanolamide.

Comparative Example 2

Ointment

An ointment was prepared in a similar manner as in Example 2 except for the exclusion of lauric acid diethanolamide and coconut fatty acid diethanolamide.

Comparative Example 3

Cataplasm

A cataplasm was prepared in a similar manner as in Example 3 except for the exclusion of coconut fatty acid diethanolamide.

Experiment 1

Stability Evaluation Study on Compositions

The composition obtained in each of the above-described Examples and Comparative Examples was stored under refrigeration at 4° C. for 3 months, and its stability was ranked based on the state of formation of crystals. The results are presented in Table 1.

TABLE 1

| Test compositions | Ranking* |
|---|---|
| Example 1 | A |
| Example 2 | A |
| Example 3 | A |
| Example 4 | A |
| Example 5 | A |
| Example 6 | A |
| Example 7 | A |
| Example 8 | A |
| Comp. Ex. 1 | D |
| | (Crystals formed from immediately after preparation) |
| Comp. Ex. 2 | D |
| | (Crystals formed from immediately after preparation) |
| Comp. Ex. 3 | D |
| | (Crystals formed from immediately after preparation) |

* Ranking standards:

| Ranking | Description |
|---|---|
| A | Formation of crystals was not observed at all. |
| B | Formation of crystals was slightly observed. |
| C | Formation of crystals was fairly observed. |
| D | Formation of crystals was significantly observed. |

From the above results, it has been found that the external preparation composition according to the present invention contains diclofenac sodium in a form dissolved in its base and has good stability.

Experiment 2

Percutaneous Absorption Study on Compositions An experiment was conducted to determine the percutaneous permeation and absorption of the composition obtained in each of Example 3 and Comparative Example 3.

(1) Percutaneous Permeation Study

The dorsal skin of a rat was excised and used as a penetration membrane. Using a Franz-type diffusion cell (penetration area diameter: 15 mm), percutaneous permeation was tested. The permeation was determined based on a cumulative permeated amount of diclofenac sodium on a receptor side. As samples, about 2 g portions of the gels prepared in Example 3 and Comparative Example 3, respectively, were used without spreading them on non-woven fabrics.

Cumulative permeated amounts ($\mu g/cm^2$) of diclofenac sodium along the passage of time are presented in Table 2.

TABLE 2

| | Cumulative penetrated amount ($\mu g/cm^2$) | | | |
|---|---|---|---|---|
| | 2 hrs | 4 hrs | 7 hrs | 10 hrs |
| Composition of Example 3 | 4.8 | 25.8 | 92 | 155.9 |
| Composition of Comp. Ex. 3 | 0.2 | 3.1 | 8.3 | 20.4 |

(2) Percutaneous Absorption Study on Rats

One day before the experiment, the hair on a dorsal part of each 6-weeks old Wistar male rat was cut off by a hair clipper. About 3 g of a cataplasm, which had been prepared in accordance with the formula of Example 3 or Comparative Example 3, were administered onto the dorsal skin of the rat in an area of 5 cm×4 cm. The cataplasm was fixed by applying taping tapes over its non-woven fabric. Along the passage of time, blood samples were collected from each rat and the concentrations of diclofenac sodium in the blood samples were measured by HPLC.

Changes in the blood concentration ($\mu g/ml$) of diclofenac sodium along the passage of time are presented in Table 3.

TABLE 3

| | Blood concentration ($\mu g/ml$) | | | |
|---|---|---|---|---|
| | 2 hrs | 4 hrs | 8 hrs | 12 hrs |
| Composition of Example 3 | 2.27 | 4.29 | 5.60 | 6.46 |
| Composition of Comp. Ex. 3 | 0.10 | 0.43 | 0.47 | 0.39 |

From the above results, it has been proven that the external preparation composition according to the present invention is a composition having high percutaneous penetration and percutaneous absorption of the active ingredient.

Capability of Exploitation in Industry

According to the external preparation composition of the present invention, it is possible to obtain an external diclofenac preparation composition which permits excellent absorption of a water-soluble salt of diclofenac while maintaining the salt highly soluble and stable in the composition.

We claim:

1. An external preparation composition comprising 0.05 to 5 wt. % of a water-soluble salt of diclofenac, 0.01 to 10 wt. % of a fatty acid dialkylolamide and water, and having a pH of from 7 to 9.

2. The external preparation composition according to claim 1, wherein the fatty acid moiety of said fatty acid dialkylolamide is coconut oil fatty acid, palm kernel oil fatty acid, stearic acid, lauric acid, oleic acid, linoleic acid or isostearic acid, and the alkylolamide moiety is diethanolamine or diisopropanolamine.

3. The external preparation composition according to claim 1, further comprising a polyhydric alcohol.

4. The external preparation composition according to claim 3, wherein said polyhydric alcohol is selected from the group consisting of propylene glycol, 1,3-butylene glycol, glycerin, sorbitol and mannitol.

5. The external preparation composition according to claim 1, further comprising a hydrophilic polymer.

6. The external preparation composition according to claim 5, wherein said hydrophilic polymer is selected from the group consisting of carboxymethylcellulose and salts thereof, polyacrylic acid and salts thereof, carboxyvinyl polymers and salts thereof, alginic acid and salts thereof, propylene glycol alginate, chitosan, hydroxypropylcellulose, hydroxypropylmethylcellulose, hydroxyethylcellulose, ethylcellulose, methylcellulose, polyvinyl alcohol, polyvinyl pyrrolidone, N-vinylacetoamide polymer, polyethylene glycol, pluronic, gelatin, methyl vinyl ether-maleic anhydride copolymer, soluble starch, pullulan and a copolymer of methyl acrylate and 2-ethyl-hexyl acrylate.

7. The external preparation composition according to claim 5, wherein said hydrophilic polymer is sodium polyacrylate.

8. The external preparation composition according to claims 1, which is a solution, cream or ointment.

9. A cataplasm comprising the external preparation composition according to claims 6 spread over a backing.

* * * * *